(12) United States Patent
Defossa et al.

(10) Patent No.: US 8,003,668 B2
(45) Date of Patent: Aug. 23, 2011

(54) AMINO-SUBSTITUTED 8-N-BENZIMIDAZOLES AND METHODS FOR THEIR USE IN BLOOD SUGAR DISORDERS

(75) Inventors: Elisabeth Defossa, Idstein (DE); Karl Schoenafinger, Alzenau (DE); Gerhard Jaehne, Frankfurt (DE); Christian Buning, Bonn (DE); Georg Tschank, Essenheim (DE); Ulrich Werner, Miehlen (DE)

(73) Assignee: Sanofi-Aventis, Paris (FR)

( * ) Notice: Subject to any disclaimer, the term of this patent is extended or adjusted under 35 U.S.C. 154(b) by 937 days.

(21) Appl. No.: 11/855,231

(22) Filed: Sep. 14, 2007

(65) Prior Publication Data

US 2008/0090870 A1    Apr. 17, 2008

Related U.S. Application Data

(63) Continuation of application No. PCT/EP2006/002057, filed on Mar. 7, 2006.

(30) Foreign Application Priority Data

Mar. 19, 2005  (DE) .......................... 10 2005 012 875

(51) Int. Cl.
*A61K 31/445* (2006.01)
*C07D 401/00* (2006.01)
(52) U.S. Cl. ........................................ 514/322; 546/199
(58) Field of Classification Search ................ 514/322; 546/199
See application file for complete search history.

(56) References Cited

FOREIGN PATENT DOCUMENTS

| EP | 1069124 | 1/2001 |
|----|---------|--------|
| WO | WO 97/12615 | 4/1997 |
| WO | WO 03/104233 | 12/2003 |

OTHER PUBLICATIONS

Setoi et al. "preparation of heteocy . . . " CA 131:116236 (1999).*
Baradi et al. "Novel 8-heterocycl . . . " Exp. Opin.Drg. Dis. 2(9) 1161-1183 (2007).*
Gupta et al. "Emerging drug . . . " Cur. Drug. target 10, 71-87 (2009).*
McIntosh et al. "application of DPP IV . . . " Int. J. Biochem. Cell Biol. 38, p. 860-872 (2006).*
Hypoglycemia Wikipedia p. 1-12 from internet (2010)I.*
Sitagliptin Wikipedia p. 1-3 (2010).*
Jordan, V. C. Nature Reviews: Drug Discovery, 2, pp. 205-213 (2003).*

* cited by examiner

*Primary Examiner* — Celia Chang
(74) *Attorney, Agent, or Firm* — Scully, Scott, Murphy & Presser, P.C.

(57) ABSTRACT

The present invention comprises the use of amino-substituted 8-N-benzimidazoles compounds of formula I

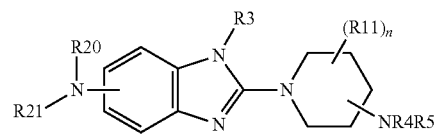

wherein R3, R4-R5, R11 and R20-R21 are hereinafter defined which display a therapeutically utilizable blood sugar-lowering action. These compounds are intended to be particularly suitable in the treatment of diabetes.

2 Claims, No Drawings

AMINO-SUBSTITUTED 8-N-BENZIMIDAZOLES AND METHODS FOR THEIR USE IN BLOOD SUGAR DISORDERS

CROSS-REFERENCE TO RELATED APPLICATIONS

This application is a continuation of International Patent Application No. PCT/EP2006/002057 filed on Mar. 7, 2006 which is incorporated herein by reference in its entirety which also claims the benefit of priority of German patent application Ser. No. 10/200,5012875.0 filed on Mar. 19, 2005.

FIELD OF THE INVENTION

The present invention relates generally to pharmaceutical compounds and compositions comprising them for the treatment of metabolic blood serum disorders and the physiological manifestations thereof. More specifically, the present invention relates to pharmaceutical compounds and compositions comprising them for the treatment of metabolic blood glucose disorders such as diabetes, hypoglycemia, hyperglycemia, hyperlipidemia, hypercholesterolemia and the like. More specifically, the present invention relates to amino-substituted 8-N-benzimidazoles and derivatives thereof for the treatment of blood glucose disorders.

BACKGROUND OF THE INVENTION

The present invention comprises the use of amino-substituted 8-N-benzimidazoles and the physiologically compatible salts thereof for producing a pharmaceutical composition for the treatment of blood sugar disorders. These compounds are particularly useful in the reduction of blood sugar and, more specifically, in the therapeutic treatment of diabetes. The use of related or similar compounds has been known and described in the prior art as follows. EP 1069124 describes 2-benzimidazolylamines as ORL-1 receptor agonists. WO 97/12615 describes benzimidazole derivatives as 15-LO inhibitors and WO 02/04425 describes structurally similar virus polymerase inhibitors.

SUMMARY OF THE INVENTION

The present invention comprises the use of amino-substituted 8-N-benzimidazoles compounds of formula I

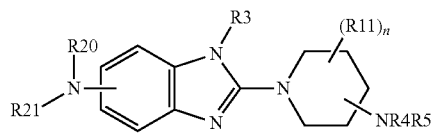

I wherein R3, R4-R5, R11 and R20-R21 are hereinafter defined which display a therapeutically utilizable blood sugar-lowering action. These compounds are intended to be particularly suitable in the treatment of diabetes.

DETAILED DESCRIPTION OF THE INVENTION

The present invention relates to carboxamide derivative compounds of the formula I, below:

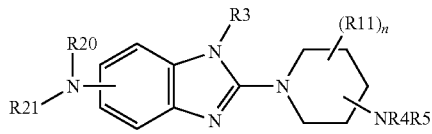

in which
R20 and R21 are each independently selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl, heterocycle, $(C_1\text{-}C_6)$-alkylene-$(C_6\text{-}C_{10})$-aryl, $(C_1\text{-}C_6)$-alkylene-$(C_6\text{-}C_{10})$-heterocycle or $S(O)_2$-aryl, where the alkyl, cycloalkyl, alkenyl, alkynyl, alkylene, aryl and heterocycle groups may each be mono- or polysubstituted by F, Cl, Br, I, CN, $NO_2$, SH, OH, $(C_1\text{-}C_6)$-alkyl, O—$(C_1\text{-}C_6)$-alkyl or S—$(C_1\text{-}C_6)$-alkyl;

R3 is selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl or heterocycle, wherein the alkyl, cycloalkyl, alkenyl, alkynyl, aryl and heterocycle groups may each be mono- or polysubstituted by F, Cl, Br, I, CN, $NO_2$, SH, OH, $(C_1\text{-}C_6)$-alkyl, —$CF_3$, —$OCF_3$, —$SCF_3$, $(C_2\text{-}C_6)$-alkenyl, $(C_2\text{-}C_6)$-alkynyl, OR7, $OP(O)(OR7)_2$, NR7R8, NR7CONR7R8, COR7, OCOR7, O—COOR7, COOR7, CONR7R8, OCONR7R8, $(C_1\text{-}C_6)$-alkylene-OR7, $(C_1\text{-}C_6)$-alkylene-NR7R8, $(C_1\text{-}C_6)$-alkylene-NR7S$(O)_2$R7, $(C_1\text{-}C_6)$-alkylene-SR7, $(C_1\text{-}C_6)$-alkylene-S(O)R7, $(C_1\text{-}C_6)$-alkylene-S$(O)_2$R7, $(C_1\text{-}C_6)$-alkylene-S$(O)_2$NR7R8, $(C_1\text{-}C_6)$-alkylene-COR7, $(C_1\text{-}C_6)$-alkylene-COOR7, $(C_1\text{-}C_6)$-alkylene-CONR7R8, SR7, S(O)R7, $S(O)_2$R7, $S(O)_2$NR7R8, NR7S$(O)_2$R7, $(C_1\text{-}C_6)$-alkylene-$(C_3\text{-}C_{10})$-cycloalkyl, $(C_1\text{-}C_6)$-alkylene-$(C_6\text{-}C_{10})$-aryl, $(C_1\text{-}C_6)$-alkylene-heterocycle, $(C_3\text{-}C_{10})$-cycloalkyl, $(C_6\text{-}C_{10})$-aryl or heterocycle;

R7 and R8 are each independently selected from the group consisting of H, $(C_1\text{-}C_6)$-alkyl, —$CF_3$, $(C_3\text{-}C_{10})$-cycloalkyl, $(C_6\text{-}C_{10})$-aryl, heterocycle, $(C_1\text{-}C_6)$-alkylene-CONR9R10, CONR9R10, $(C_1\text{-}C_6)$-alkylene-COOR9, COOR9, COR9, $(C_1\text{-}C_6)$-alkylene-COR9, $(C_1\text{-}C_6)$-alkylene-OR9, $(C_1\text{-}C_6)$-alkylene-NR9R10, $(C_1\text{-}C_6)$-alkylene-SR9, $(C_1\text{-}C_6)$-alkylene-S(O)R9, $(C_1\text{-}C_6)$-alkylene-S$(O)_2$R9, S(O)R9, $S(O)_2$R9, $(C_1\text{-}C_4)$-alkylene-$(C_6\text{-}C_{10})$-aryl and $(C_1\text{-}C_4)$-alkylene-heterocycle;

R9 and R10 are each independently selected from the group consisting of H, $(C_1\text{-}C_6)$-alkyl, $(C_1\text{-}C_6)$-alkylene-$(C_6\text{-}C_{10})$-aryl, —$(C_6\text{-}C_{10})$-aryl, heterocycle and $(C_1\text{-}C_6)$-alkylene-heterocycle;

R4 and R5 are each independently selected from the group consisting of H, $(C_1\text{-}C_6)$-alkyl or $(C_3\text{-}C_8)$-cycloalkyl, where $(C_1\text{-}C_6)$-alkyl and $(C_3\text{-}C_8)$-cycloalkyl may be substituted by F, Cl, Br, I, CN, aryl, heterocycle, $NH_2$, $NH(C_1\text{-}C_6)$-alkyl, $N((C_1\text{-}C_6)\text{-alkyl})_2$, OH, $O(C_1\text{-}C_6)$-alkyl, O-aryl, O-heteroaryl, $S(C_1\text{-}C_6)$-alkyl, $S(O)(C_1\text{-}C_6)$-alkyl and $S(O)_2(C_1\text{-}C_6)$-alkyl, where these alkyl groups may in turn be substituted by F, Cl, Br or I;

R11 is selected from the group consisting of F, Cl, Br, I, $(C_1\text{-}C_6)$-alkyl, $(C_3\text{-}C_8)$-cycloalkyl, $NH_2$, $NH(C_1\text{-}C_6)$-alkyl, $NH(C_3\text{-}C_7)$-cycloalkyl, $N((C_1\text{-}C_6)\text{-alkyl})_2$ and O—$(C_1\text{-}C_6)$-alkyl, where the alkyl groups may be mono- or polysubstituted by F, Cl, Br or I;

n is 0, 1 or 2;

and the pharmaceutically acceptable salts thereof useful in the preparation of a pharmaceutical composition for the reduction of blood sugar levels.

Preferably, the present invention comprises the use of the compounds of the formula I in which one or more of the substituents are defined as follows R20 and R21 are each independently selected from the group consisting of H, $(C_1$-$C_{10})$-alkyl, $(C_3$-$C_{10})$-cycloalkyl, $(C_2$-$C_{10})$-alkenyl, $(C_2$-$C_{10})$-alkynyl, $(C_6$-$C_{10})$-aryl, heterocycle, $(C_1$-$C_6)$-alkylene-$(C_6$-$C_{10})$-aryl, $(C_1$-$C_6)$-alkylene-$(C_6$-$C_{10})$-heterocycle and $S(O)_2$-aryl, where the alkyl, cycloalkyl, alkenyl, alkynyl, alkylene, aryl and heterocycle groups may each be mono- or polysubstituted by F, Cl, Br, I, CN, $NO_2$, SH, OH, $(C_1$-$C_6)$-alkyl, O—$(C_1$-$C_6)$-alkyl or S—$(C_1$-$C_6)$-alkyl;

R3 is selected from the group consisting of $(C_2$-$C_{10})$-alkenyl and $(C_1$-$C_6)$-alkylene-$(C_6$-$C_{10})$-aryl;

R4 and R5 are each independently selected from the group consisting of H, $(C_1$-$C_6)$-alkyl and $(C_3$-$C_8)$-cycloalkyl, where $(C_1$-$C_6)$-alkyl or $(C_3$-$C_8)$-cycloalkyl may be substituted by F, Cl, Br, I, CN, aryl, heterocycle, $NH_2$, $NH(C_1$-$C_6)$-alkyl, $N((C_1$-$C_6)$-alkyl$)_2$, OH, O$(C_1$-$C_6)$-alkyl, O-aryl, O-heteroaryl, $S(C_1$-$C_6)$-alkyl, $S(O)(C_1$-$C_6)$-alkyl or $S(O)_2$ $(C_1$-$C_6)$-alkyl, where these alkyl groups may in turn be substituted by F, Cl, Br or I;

n is 0;

and the pharmaceutically acceptable salts thereof for the preparation of a composition for lowering blood sugar.

More particularly preferred are those compounds of formula I in which the previously defined substituents are each specified as follows:

R20 and R21 are each independently selected from the group consisting of H, $(C_1$-$C_6)$-alkylene-$(C_6$-$C_{10})$-aryl and $S(O)_2$-aryl, where the aryl groups may each be mono- or polysubstituted by F, Cl, Br, I, CN, $NO_2$, SH, OH, $(C_1$-$C_6)$-alkyl, O—$(C_1$-$C_6)$-alkyl or S—$(C_1$-$C_6)$-alkyl;

R3 is selected from the group consisting of $(C_2$-$C_{10})$-alkenyl and $(C_1$-$C_6)$-alkylene-$(C_6$-$C_{10})$-aryl;

R4 and R5 are each H;

n is 0;

and the pharmaceutically acceptable salts thereof for the preparation of a composition for lowering blood sugar.

The present invention also comprises use of the compounds of the formula I in the form of their racemates, racemic mixtures, pure enantiomers, their diastereomers and mixtures thereof.

When radicals or substituents can occur more than once in the compounds of the formula I, they may all each independently have the definitions specified and be the same or different.

Owing to their higher water solubility, pharmaceutically acceptable salts are particularly suitable for medical applications compared to the starting or base compounds. These salts must have a pharmaceutically acceptable anion or cation. Suitable pharmaceutically acceptable acid addition salts of the inventive compounds are salts of inorganic acids such as hydrochloric acid, hydrobromic acid, phosphoric acid, metaphosphoric acid, nitric acid and sulfuric acid, and organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1, 3-propanediol), diethanolamine, lysine or ethylenediamine.

Salts with a pharmaceutically unacceptable anion, for example trifluoroacetate, are likewise included in the scope of the invention as useful intermediates for the preparation or purification of pharmaceutically acceptable salts and/or for the use in non-therapeutic, for example in vitro, applications.

The term "physiologically functional derivative" used here refers to any physiologically compatible derivative of an inventive compound of the formula I, for example an ester which, on administration to a mammal, for example the human, is capable (directly or indirectly) of forming a compound of the formula I or an active metabolite thereof.

The physiologically functional derivatives also include prodrugs of the inventive compounds. Such prodrugs can be metabolized in vivo to give an inventive compound. These prodrugs may or may not themselves be active.

The inventive compounds may also be present in various polymorphic forms, for example as amorphous and crystalline polymorphic forms. All polymorphic forms of the inventive compounds are included within the scope of the invention and are a further aspect of the invention.

Hereinafter, all references to "compound(s) of the formula (I)" relate to compound(s) of the formula I as described above, and also their salts, solvates and physiologically functional derivatives as described herein.

An alkyl substituent means a straight-chain or branched hydrocarbon chain having one or more carbons, for example methyl, ethyl, isopropyl, tert-butyl, hexyl.

The alkyl substituent may be mono- or polysubstituted by suitable groups, for example:

F, Cl, Br, I, $CF_3$, $NO_2$, $N_3$, CN, COOH, COO$(C_1$-$C_6)$alkyl, $CONH_2$, CONH$(C_1$-$C_6)$alkyl, CON[$(C_1$-$C_6)$alkyl]$_2$, cycloalkyl, $(C_2$-$C_6)$-alkenyl, $(C_2$-$C_6)$-alkynyl, O—$(C_1$-$C_6)$-alkyl, O—CO—$(C_1$-$C_6)$-alkyl, O—CO—$(C_1$-$C_6)$-aryl, O—CO—$(C_1$-$C_6)$-heterocycle;

$PO_3H_2$, $SO_3H$, $SO_2$—$NH_2$, $SO_2NH(C_1$-$C_6)$-alkyl, $SO_2N$ [$(C_1$-$C_6)$-alkyl]$_2$, S—$(C_1$-$C_6)$-alkyl, S—$(CH_2)_n$-aryl, S—$(CH_2)_n$-heterocycle, SO—$(C_1$-$C_6)$-alkyl, SO—$(CH_2)_n$-aryl, SO—$(CH_2)_n$-heterocycle, $SO_2$—$(C_1$-$C_6)$-alkyl, $SO_2$—$(CH_2)_n$-aryl, $SO_2$—$(CH_2)_n$-heterocycle, $SO_2$—NH $(CH_2)_n$-aryl, $SO_2$—NH$(CH_2)_n$-heterocycle, $SO_2$—N$((C_1$-$C_6)$-alkyl$)(CH_2)_n$-aryl, $SO_2$—N$((C_1$-$C_6)$-alkyl$)(CH_2)_n$-heterocycle, $SO_2$—N$((CH_2)_n$-aryl$)_2$, $SO_2$—N$((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—$(C_1$-$C_6)$-alkyl, $(C_1$-$C_6)$-alkyl or $NH_2$;

C(═NH)(NH$_2$), NH$_2$, NH—$(C_1$-$C_6)$-alkyl, N$((C_1$-$C_6)$-alkyl$)_2$, NH—CO—$(C_1$-$C_6)$-alkyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, N$((C_1$-$C_6)$-alkyl$)$-CO—$(C_1$-$C_6)$-alkyl, N$((C_1$-$C_6)$-alkyl$)$-COO—$(C_1$-$C_6)$-alkyl, N$((C_1$-$C_6)$-alkyl$)$-CO-aryl, N$((C_1$-$C_6)$-alkyl$)$-CO-heterocycle, N$((C_1$-$C_6)$-alkyl$)$-COO-aryl, N$((C_1$-$C_6)$-alkyl$)$-COO-heterocycle, N$((C_1$-$C_6)$-alkyl$)$-CO—NH—$(C_1$-$C_6)$-alkyl), N$((C_1$-$C_6)$-alkyl$)$-CO—NH-aryl, N$((C_1$-$C_6)$-alkyl$)$-CO—NH-heterocycle, N$((C_1$-$C_6)$-alkyl$)$-CO—N$((C_1$-$C_6)$-alkyl$)_2$, N$((C_1$-$C_6)$-alkyl$)$-CO—N $((C_1$-$C_6)$-alkyl$)$-aryl, N$((C_1$-$C_6)$-alkyl$)$-CO—N$((C_1$-$C_6)$-alkyl$)$-heterocycle, N$((C_1$-$C_6)$-alkyl$)$-CO—N-(aryl)$_2$, N$((C_1$-$C_6)$-alkyl$)$-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N$((C_1$-$C_6)$-alkyl$)_2$, N(heterocycle)-CO—N$((C_1$-$C_6)$-alkyl$)_2$, N(aryl)-CO—N ((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, where n may be 0-6, where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

An alkenyl substituent are those straight-chain or branched hydrocarbon chains having two or more carbons and one or more double bonds, for example vinyl, allyl, pentenyl, 2-methyl-but-2-en-4-yl.

The alkenyl substituent may be mono- or polysubstituted by suitable groups, for example:

F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$;

C(=NH)(NH$_2$), NH$_2$, NH—(C$_1$-C$_6$)-alkyl, N((C$_1$-C$_6$)-alkyl)$_2$, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-COO—(C$_1$-C$_6$)-alkyl, N((C$_1$-C$_6$)-alkyl)-CO-aryl, N((C$_1$-C$_6$)-alkyl)-CO-heterocycle, N((C$_1$-C$_6$)-alkyl)-COO-aryl, N((C$_1$-C$_6$)-alkyl)-COO-heterocycle, N((C$_1$-C$_6$)-alkyl)-CO—NH—(C$_1$-C$_6$)-alkyl), N((C$_1$-C$_6$)-alkyl)-CO—NH-aryl, N((C$_1$-C$_6$)-alkyl)-CO—NH-heterocycle, N((C$_1$-C$_6$)-alkyl)-CO—N((C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N((C$_1$-C$_6$)-alkyl)$_2$, N(heterocycle)-CO—N((C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, where n may be 0-6, where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

An alkynyl substituent is understood to mean a straight-chain or branched hydrocarbon chain having two or more carbons and one or more triple bonds, for example ethynyl, propynyl, butynyl, hexynyl.

The alkynyl substituents may be mono- or polysubstituted by suitable groups, for example:

F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$;

C(=NH)(NH$_2$), NH$_2$, NH—(C$_1$-C$_6$)-alkyl, N((C$_1$-C$_6$)-alkyl)$_2$, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-COO—(C$_1$-C$_6$)-alkyl, N((C$_1$-C$_6$)-alkyl)-CO-aryl, N((C$_1$-C$_6$)-alkyl)-CO-heterocycle, N((C$_1$-C$_6$)-alkyl)-COO-aryl, N((C$_1$-C$_6$)-alkyl)-COO-heterocycle, N((C$_1$-C$_6$)-alkyl)-CO—NH—(C$_1$-C$_6$)-alkyl), N((C$_1$-C$_6$)-alkyl)-CO—NH-aryl, N((C$_1$-C$_6$)-alkyl)-CO—NH-heterocycle, N((C$_1$-C$_6$)-alkyl)-CO—N((C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N((C$_1$-C$_6$)-alkyl)$_2$, N(heterocycle)-CO—N((C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, where n may be 0-6, where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

An aryl substituent is understood to mean a phenyl, naphthyl, biphenyl, tetrahydronaphthyl, alpha- or beta-tetralonyl, indanyl or indan-1-onyl radical.

The aryl substituents may be mono- or polysubstituted by suitable groups, for example:

F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$- heterocycle, $SO_2$—$N((CH_2)_n$-aryl$)_2$, $SO_2$—$N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2)_n$-aryl and O—($CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

A cycloalkyl substituent means a ring system which comprises one or more rings and is present in saturated or partially unsaturated form (with one or two double bonds), and is formed exclusively from carbon atoms, for example cyclopropyl, cyclopentyl, cyclopentenyl, cyclohexyl or adamantyl.

The cycloalkyl substituents may be mono- or polysubstituted by suitable groups, for example:

F, Cl, Br, I, $CF_3$, $NO_2$, $N_3$, CN, COOH, COO($C_1$-$C_6$)alkyl, $CONH_2$, $CONH(C_1$-$C_6$)alkyl, $CON[(C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6$)-alkyl, $SO_2N[(C_1$-$C_6$)-alkyl]$_2$, S—($C_1$-$C_6$)-alkyl, S—($CH_2)_n$-aryl, S—($CH_2)_n$-heterocycle, SO—($C_1$-$C_6$)-alkyl, SO—($CH_2)_n$-aryl, SO—($CH_2)_n$-heterocycle, $SO_2$—($C_1$-$C_6$)-alkyl, $SO_2$—($CH_2)_n$-aryl, $SO_2$—($CH_2)_n$-heterocycle, $SO_2$—NH($CH_2)_n$-aryl, $SO_2$—NH($CH_2)_n$-heterocycle, $SO_2$—N(($C_1$-$C_6$)-alkyl)($CH_2)_n$-aryl, $SO_2$—N(($C_1$-$C_6$)-alkyl)($CH_2)_n$-heterocycle, $SO_2$—N(($CH_2)_n$-aryl)$_2$, $SO_2$—N(($CH_2)_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2)_n$-aryl and O—($CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

Heterocycle, heterocycle and heterocyclic substituents are understood to mean rings and ring systems which, apart from carbon, also contain heteroatoms, for example nitrogen, oxygen or sulfur. This definition also includes ring systems in which the heterocycle or the heterocyclic group is fused to benzene rings. The heterocycle or the heterocyclic group may be aromatic, saturated aliphatic or partially unsaturated aliphatic.

Suitable heterocycle substituents or "heterocyclic groups" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is 2-, 3- or 4-pyridyl. Thienyl is 2- or 3-thienyl. Furyl is 2- or 3-furyl.

Also included are the corresponding N-oxides of these compounds, i.e., for example, 1-oxy-2-, -3- or -4-pyridyl.

Also included are mono- or polybenzo fused derivatives of these heterocycles.

The heterocyclic rings or heterocyclic radicals may be mono- or polysubstituted by suitable groups, for example: F, Cl, Br, I, $CF_3$, $NO_2$, $N_3$, CN, COOH, COO($C_1$-$C_6$)alkyl, $CONH_2$, $CONH(C_1-C_6)alkyl$, $CON[(C_1-C_6)alkyl]_2$, cycloalkyl, $(C_2-C_6)$-alkenyl, $(C_2-C_6)$-alkynyl, $O-(C_1-C_6)$-alkyl, $O-CO-(C_1-C_6)$-alkyl, $O-CO-(C_1-C_6)$-aryl, $O-CO-(C_1-C_6)$-heterocycle;

$PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, $SO_2-N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, $O-(C_1-C_6)$-alkyl, $(C_1-C_6)$-alkyl or $NH_2$;

$C(=NH)(NH_2)$, $NH_2$, $NH-(C_1-C_6)$-alkyl, $N((C_1-C_6)$-alkyl$)_2$, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N((C_1-C_6)$-alkyl$)-CO-(C_1-C_6)$-alkyl, $N((C_1-C_6)$-alkyl$)-COO-(C_1-C_6)$-alkyl, $N((C_1-C_6)$-alkyl$)-CO$-aryl, $N((C_1-C_6)$-alkyl$)-CO$-heterocycle, $N((C_1-C_6)$-alkyl$)-COO$-aryl, $N((C_1-C_6)$-alkyl$)-COO$-heterocycle, $N((C_1-C_6)$-alkyl$)-CO-NH-(C_1-C_6)$-alkyl$)$, $N((C_1-C_6)$-alkyl$)-CO-NH$-aryl, $N((C_1-C_6)$-alkyl$)-CO-NH$-heterocycle, $N((C_1-C_6)$-alkyl$)-CO-N((C_1-C_6)$-alkyl$)_2$, $N((C_1-C_6)$-alkyl$)-CO-N((C_1-C_6)$-alkyl$)$-aryl, $N((C_1-C_6)$-alkyl$)-CO-N((C_1-C_6)$-alkyl$)$-heterocycle, $N((C_1-C_6)$-alkyl$)-CO-N$-(aryl$)_2$, $N((C_1-C_6)$-alkyl$)-CO-N$-(heterocycle$)_2$, $N(aryl)-CO-(C_1-C_6)$-alkyl, $N(heterocycle)-CO-(C_1-C_6)$-alkyl, $N(aryl)-COO-(C_1-C_6)$-alkyl, $N(heterocycle)-COO-(C_1-C_6)$-alkyl, $N(aryl)-CO$-aryl, $N(heterocycle)-CO$-aryl, $N(aryl)-COO$-aryl, $N(heterocycle)-COO$-aryl, $N(aryl)-CO-NH-(C_1-C_6)$-alkyl$)$, $N(heterocycle)-CO-NH-(C_1-C_6)$-alkyl$)$, $N(aryl)-CO-NH$-aryl, $N(heterocycle)-CO-NH$-aryl, $N(aryl)-CO-N((C_1-C_6)$-alkyl$)_2$, $N(heterocycle)-CO-N((C_1-C_6)$-alkyl$)_2$, $N(aryl)-CO-N((C_1-C_6)$-alkyl$)$-aryl, $N(heterocycle)-CO-N((C_1-C_6)$-alkyl$)$-aryl, $N(aryl)-CO-N$-(aryl$)_2$, $N(heterocycle)-CO-N$-(aryl$)_2$, aryl, $O-(CH_2)_n$-aryl and $O-(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl or $CONH_2$.

The compound(s) of the formula (I) may also be administered in combination with further active ingredients.

The amount of a compound of the formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 ng, typically from 1 ng to 10 mg, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of the formula I may be used for therapy of the abovementioned conditions as the compounds themselves, although they are preferably in the form of a pharmaceutical composition with an acceptable carrier. The carrier of course, has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of the formula I. The inventive pharmaceutical compositions may be produced by one of the known pharmaceutical methods which consist essentially in mixing the constituents with pharmacologically acceptable carriers and/or excipients.

Inventive pharmaceutical compositions are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of the formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of the formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration include preferably sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa butter, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986).

The compounds of the formula I may be administered alone or else also in combination with further active ingredients. Further useful active ingredients for combination products are as follows:

All antidiabetics mentioned in the Rote Liste 2001, chapter 12. They can be combined with the inventive compounds of the formula I, in particular for synergistic enhancement of action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Antidiabetics include insulin and insulin derivatives, for example Lantus® (see www.lantus.com) or Apidra®, fast-acting insulins (see U.S. Pat. No. 6,221,633), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells (PPAR=peroxisome proliferator-activated receptor, PXR=pregnane X receptor, ATP=adenosine triphosphate).

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin (HMG-CoA=3-hydroxy-3-methylglutaryl coenzyme A).

In one embodiment of the invention, the compounds of the formula I are administered in combination with a cholesterol absorption inhibitor, for example, ezetimibe, tiqueside, pamaqueside, or with a compound as described in PCT/EP 2004/00269, WO 2004/000804, WO 2004/000803, WO 2004/000805, EP 0114531, U.S. Pat. No. 6,498,156.

In one embodiment of the invention, the compounds of the formula I are administered in combination with a PPAR gamma agonist, for example, rosiglitazone, pioglitazone, JTT-501, GI 262570.

In one embodiment of the invention, the compounds of the formula I are administered in combination with PPAR alpha agonist, for example, GW 9578, GW 7647.

In one embodiment of the invention, the compounds of the formula I are administered in combination with a mixed PPAR alpha/gamma agonist, for example, GW 1536, AVE 8042, AVE 8134, AVE 0847, or as described in WO 00/64888, WO 00/64876, DE10142734.4.

In one embodiment of the invention, the compounds of the formula I are administered in combination with a fibrate, for example fenofibrate, clofibrate, bezafibrate.

In one embodiment of the invention, the compounds of the formula I are administered in combination with an MTP inhibitor, for example implitapide, BMS-201038, R-103757 (MTP=microsomal triglyceride transfer protein).

In one embodiment of the invention, the compounds of the formula I are administered in combination with bile acid absorption inhibitor (see, for example, U.S. Pat. Nos. 6,245,744 or 6,221,897), for example HMR 1741.

In one embodiment of the invention, the compounds of the formula I are administered in combination with a CETP inhibitor, for example JTT-705 (CETP=cholesteryl ester transfer protein).

In one embodiment of the invention, the compounds of the formula I are administered in combination with a polymeric bile acid adsorber, for example cholestyramine, colesevelam.

In one embodiment of the invention, the compounds of the formula I are administered in combination with an LDL receptor inducer (see U.S. Pat. No. 6,342,512), for example HMR1171, HMR1586 (LDL=low-density lipids).

In one embodiment of the invention, the compounds of the formula I are administered in combination with an ACAT inhibitor, for example avasimibe (ACAT=acyl-coenzyme A:cholesterol acyl transferase).

In one embodiment of the invention, the compounds of the formula I are administered in combination with an antioxidant, for example OPC-14117.

In one embodiment of the invention, the compounds of the formula I are administered in combination with a lipoprotein lipase inhibitor, for example NO-1886.

In one embodiment of the invention, the compounds of the formula I are administered in combination with an ATP citrate lyase inhibitor, for example SB-204990.

In one embodiment of the invention, the compounds of the formula I are administered in combination with a squalene synthetase inhibitor, for example BMS-188494.

In one embodiment of the invention, the compounds of the formula I are administered in combination with a lipoprotein (a) antagonist, for example CI-1027 or nicotinic acid.

In one embodiment of the invention, the compounds of the formula I are administered in combination with a lipase inhibitor, for example orlistat.

In one embodiment of the invention, the compounds of the formula I are administered in combination with insulin.

In one embodiment, the compounds of the formula I are administered in combination with a sulfonylurea, for example tolbutamide, glibenclamide, glipizide or glimepiride.

In one embodiment, the compounds of the formula I are administered in combination with a biguanide, for example metformin.

In yet another embodiment, the compounds of the formula I are administered in combination with a meglitinide, for example repaglinide.

In one embodiment, the compounds of the formula I are administered in combination with a thiazolidinedione, for example troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, for example miglitol or acarbose.

In one embodiment, the compounds of the formula I are administered in combination with adenosine A1 agonists, for example those which are described in WO 2004/003002.

In one embodiment, the compounds of the formula I are administered in combination with an active ingredient which acts on the ATP-dependent potassium channel of the beta cells, for example tolbutamide, glibenclamide, glipizide, glimepiride or repaglinide.

In one embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists (NPY=neuropeptide Y, e.g. naphthalene-1-sulfonic acid {4-[(4-aminoquinazolin-2-ylamino)methyl]cyclohexylmethyl}amide hydrochloride (CGP 71683A)), MC4 agonists (MC4=melanocortin 4 receptor, e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (H3=histamine receptor, e.g. 3-cyclohexyl-1-(4,4-dimethyl-1,4,6,7-tetrahydroimidazo[4,5-c]pyridin-5-yl)propan-1-one oxalic acid salt (WO 00/63208)); TNF agonists (TNF=tumor necrosis factor), CRF antagonists (CRF=corticotropin releasing factor, e.g. [2-methyl-9-(2,4,6-trimethylphenyl)-9H-1,3,9-triazafluoren-4-yl]dipropylamine (WO 00/66585)), CRF BP antagonists (CRF BP=corticortropin releasing factor binding protein, e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients specified in WO 02/28346), MSH (melanocyte-stimulating hormone) agonists, CCK-A (CCK-A=cholecystokinin-A) agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists (serotonin mimetics), e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tert-butyl ester (WO 01/85695)), TRH agonists (TRH=TSH releasing hormone; TSH=thyroid-stimulating hormone; thyrotropin), see, for example, EP 0 462 884, uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (DA=dopamine autoreceptor, for example bromocriptine, doprexin), lipase/amylase inhibitors (e.g. WO 00/40569), PPAR modulators (e.g. WO 00/78312), RXR (RXR=retinoid X receptor) modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In yet another embodiment, the other active ingredient is sibutramine.

In one embodiment, the other active ingredient is orlistat.

In one embodiment, the other active ingredient is mazindol or phentermine.

In another embodiment, the other active ingredient is rimonabant.

In one embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230-6.); Caromax is a carob-containing product supplied by Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of foodstuffs, for example, in bakery products or muesli bars.

The compounds useful in the methods of the present invention may be formulated as combination compositions comprised of any two or more of the above-mentioned compounds and optionally one or more further pharmacologically active substances as described below and these combination compositions must also be regarded as falling within the scope of the claims that define the present invention recited below.

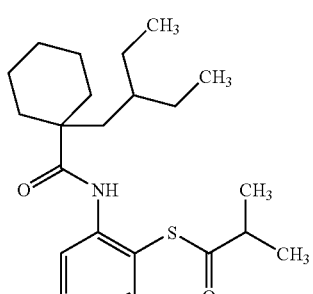
JTT-705

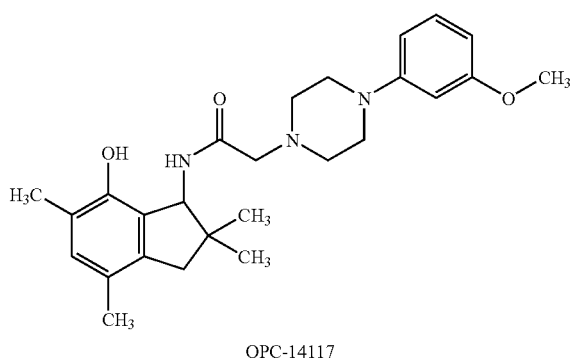
OPC-14117

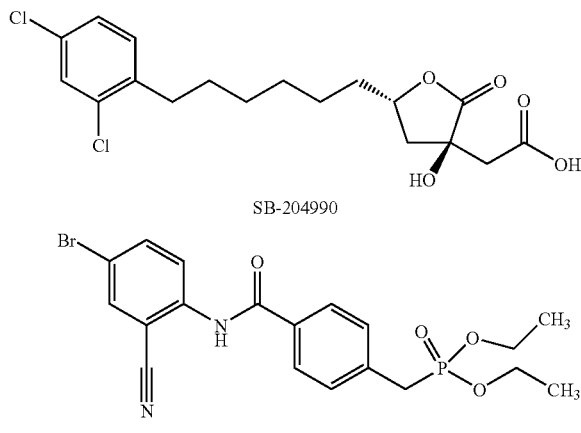
SB-204990

NO-1886

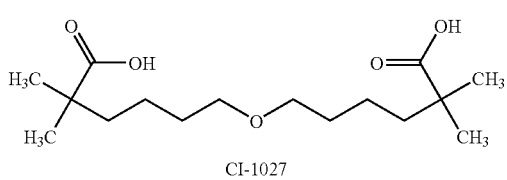
CI-1027

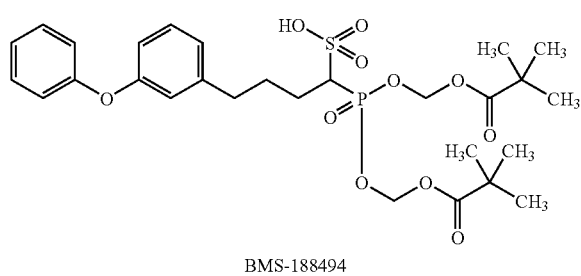
BMS-188494

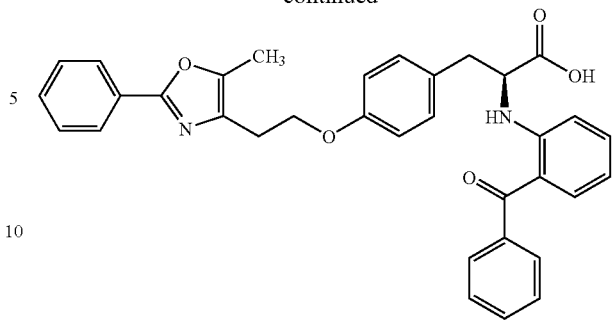
GI 262570

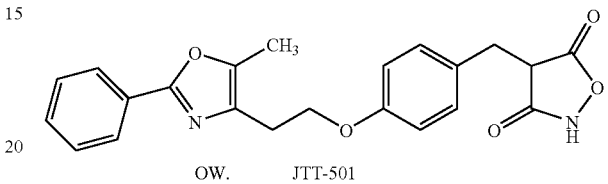
JTT-501

The compounds of the formula I can be prepared by reacting suitable starting materials of the formula II in which X is a leaving group, such as chlorine, bromine, iodine, sulfonyloxy, sulfinyl or sulfoxyl, with a compound of the formula IV optionally in the presence of suitable bases and in suitable solvents.

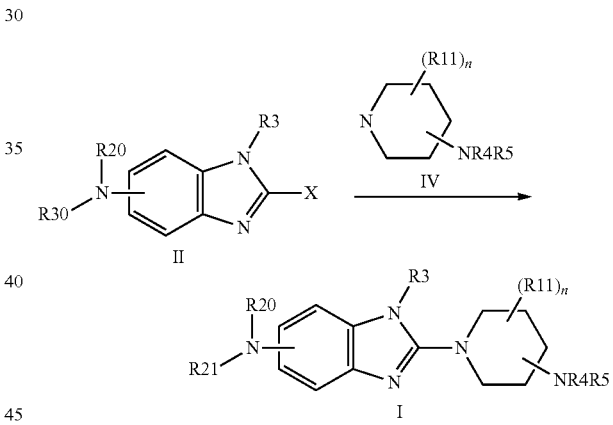

In the cases where R4 and R5 are both hydrogen, it may be appropriate to use the radical IV in a form protected on the nitrogen function and to detach the protecting group again on completion of reaction with II. Such suitable protecting groups and the processes for their introduction and detachment are known (see: Theodora W. Greene and Peter G. M. Wuts, Protective Groups in Organic Synthesis, 3rd Edition, John Wiley & Sons, Inc., New York, 1999).

The halogen compounds of the formula II can be obtained by known processes, for example by halogenating the corresponding H, hydroxyl or thio compound (formula II, X=H, OH or SH). Suitable halogenating agents may, by way of example, be halogens such as chlorine and bromine, N-bromosuccinimide, phosphorus pentachloride or phosphorus oxychloride.

The synthesis of compounds of the formula II is described in the literature. They may be prepared, for example, by condensing substituted diaminobenzene derivatives with aldehydes in the presence of an oxidizing agent (for example atmospheric oxygen, oxygen, iodine, oxone, quinones, peroxides, etc.), or alternatively with carboxylic acids, nitriles or amides, without or in the presence of a catalyst.

The amines IV can be synthesized by processes known from the literature. Some derivatives of the formula IV, for example piperidin-3-ylamines, are commercially available.

The tabulated examples listed below are provided to better illustrate methods for practicing the present invention as disclosed herein. The examples are provided to better describe and more specifically set forth the compounds, processes and methods of the present invention as contemplated herein. However, it is to be recognized that they are for illustrative purposes only, and should not be interpreted as limiting the spirit and scope of the invention as later recited by the claims that follow.

TABLE 1

I

| Ex. | Position of —NR20R21 | R20 | R21 | R3 | NR4R5 | n | R11 |
|---|---|---|---|---|---|---|---|
| 1 | 6 | H | Phenyl-SO$_2$— | —CH$_2$—CH=C(CH$_3$)$_2$ | 3-R—NH$_2$ × TFA | 0 | — |
| 2 | 6 | Phenyl-SO$_2$— | Phenyl-SO$_2$— | Benzyl- | 3-R—NH$_2$ × TFA | 0 | — |
| 3 | 6 | H | 2-Cl-4-F-Benzyl- | Benzyl- | 3-R—NH$_2$ × TFA | 0 | — |
| 4 | 6 | Benzyl- | Benzyl- | Benzyl- | 3-R—NH$_2$ × TFA | 0 | — |
| 5 | 6 | 2-Cl-4-F-Benzyl- | 2-Cl-4-F-Benzyl- | Benzyl- | 3-R—NH$_2$ × TFA | 0 | — |
| 6 | 6 | H | Benzyl- | —CH$_2$—CH=C(CH$_3$)$_2$ | 3-R—NH$_2$ × TFA | 0 | — |
| 7 | 6 | H | H | —CH$_2$—CH=C(CH$_3$)$_2$ | 3-R—NH$_2$ × TFA | 0 | — |
| 8 | 6 | H | H | Benzyl- | 3-R—NH$_2$ × TFA | 0 | — |
| 9 | 5 | H | H | —CH$_2$—CH=C(CH$_3$)$_2$ | 3-R—NH$_2$ × TFA | 0 | — |

The compounds of the formula I feature favorable effects on lipid and carbohydrate metabolism; in particular, they lower the blood sugar level and are suitable for the treatment of type II diabetes, of insulin resistance, of dislipidemias and of metabolic syndrome/syndrome X. Moreover, the compounds are suitable for the treatment and prophylaxis of arteriosclerotic manifestations. The compounds can be used alone or in combination with further blood sugar-lowering active ingredients. The compounds act as DPP IV (dipeptidyl peptidase IV) inhibitors and are also suitable for the treatment of disorders of perception and other psychiatric indications, for example depressions, anxiety states, anxiety neuroses, schizophrenia, and for the treatment of disorders associated with the circadian rhythm, for weight reduction in mammals, for the treatment of immune disorders and for the treatment of drug abuse.

They are additionally suitable for the treatment of cancer, arthritis, osteoarthritis, osteoporosis, sleep disorders, sleep apnea, masculine and feminine sexual disorders, inflammations, acne, pigmentation of the skin, disorders of steroid metabolism, skin diseases, psoriasis, mycoses, neurodegenerative disorders, multiple sclerosis and Alzheimer's disease.

The efficacy of the compounds was tested as follows:
Measurement of the DPP-IV Activity:
Material:
DPP-IV from porcine kidneys (Sigma, Munich)
H-Ala-Pro-AFC (Bachem, Weil am Rhein)
Test conditions:
DPP-IV (1 mU/ml, end concentration)
H-Ala-Pro-AFC (15 µm end concentration) in Tris/HCl (40 mM, pH 7.4), total volume 0.2 ml The reaction was performed at room temperature for different periods (typically 10 minutes) and stopped at the end of the reaction by adding 20 µl of ZnCl$_2$ (1 M). The conversion of H-Ala-Pro-AFC was determined fluorimetrically by measuring the emission at 535 nm on excitation at 405 nm. In the case of addition of inhibitors, the buffer volume added was adjusted such that a total volume of the test mixture of 200 µl was maintained.

% inhibition at a fixed concentration was calculated as follows:

(1−enzyme activity$_{inhibited\ reaction}$/enzyme activity$_{uninhibited\ reaction}$)×100

IC$_{50}$ values for inhibitors were determined by varying the inhibitor concentrations at the given substrate concentration of 15 µM. K$_i$ and K$_m$ values were determined by corresponding variation of substrate and inhibitor concentration as described (Dixon, M. and Webb, E.C.(1979) Enzymes, third edition, pp. 47-206, Academic Press). The values for K$_m$, IC$_{50}$ and K$_i$ were calculated using a commercially available software package (Leatherbarrow, R. J. (1992) GraFit Version 3.0, Erithacus Software Ltd. Staines, U.K.).

TABLE 2

Biological activity of the examples:

| Example | % inhibition at 30 µm |
|---|---|
| 1 | 56 |
| 2 | 8 |
| 4 | 75 |
| 6 | 73 |
| 9 | 34 |

It can be seen from the table that the compounds of the formula I inhibit the activity of the DPP-IV (dipeptidyl peptidase IV) and are thus suitable for lowering the blood sugar level.

The preparation of some working examples will be described in detail hereinafter; the other compounds of the formula I were obtained analogously:

EXAMPLE 1

R-N-[2-(3-R-Aminopiperidin-1-yl)-1-(3-methylbut-2-enyl)-1H-benzimidazol-6-yl]-benzenesulfonamide trifluoroacetic acid salt a) 2-Bromo-5/6-nitro-1H-benzimidazole

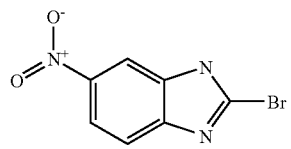

A suspension of 5.0 g (25.61 mmol) of 5/6-nitro-1H-benzimidazole-2-thiol in 30 ml of methanol and 10 ml of hydrogen bromide (48% in water) was cooled to 5-10° C. and admixed with 3.55 g (22.2 mmol) of bromine. Subsequently, the mixture was stirred at 5-10° C. for 45 minutes and admixed with 8 ml of methanol/aqueous NH$_3$ solution=3/1=. The precipitate was filtered off with suction, and the mother liquor was poured onto ice-water. This formed another precipitate, which was likewise filtered off with suction. The combined precipitates were partitioned between ethyl acetate and water, dried and concentrated under reduced pressure. 1.12 g of the desired product were obtained and were used in the next stage without further purification.

b) 2-Bromo-1-(3-methylbut-2-enyl)-5/6-nitro-1H-benzimidazole

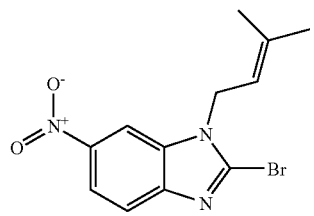

0.55 g (2.27 mmol) of 2-bromo-5/6-nitro-1H-benzimidazole was dissolved in 10 ml of dimethylformamide, admixed with 11.1 g (3.41 mmol) of cesium carbonate and stirred at room temperature for 30 minutes. 408 mg (2.50 mmol) of 1-bromo-3-methyl-2-butene was added and the reaction mixture was stirred at room temperature for 4 hours. The precipitate was filtered off with suction and washed with dimethylformamide. The filtrate was concentrated under reduced pressure and the residue was partitioned between ethyl acetate and water. The organic phase was dried and concentrated under reduced pressure. 371 mg (53%) of the desired product were obtained.

LCMS: m/z=310.0/312.0 (M+H)$^+$.

c) tert-Butyl R-{1-[1-(3-methylbut-2-enyl)-6-nitro-1H-benzimidazol-2-yl]piperidin-3-yl}carbamate

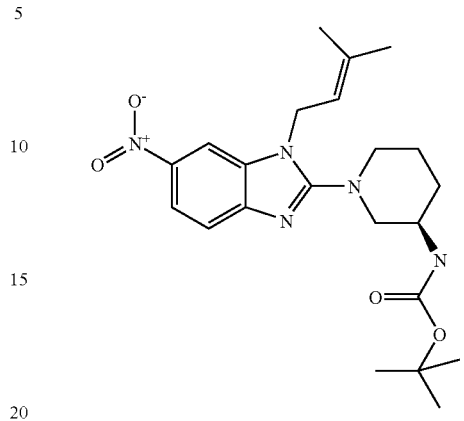

260 mg (1.29 mmol) of tert-butyl R-piperidin-3-yl carbamate were dissolved in 2 ml of dimethylformamide and admixed with 575 mg (1.77 mmol) of cesium carbonate, and stirred at room temperature for 30 minutes. 365 mg (1.18 mmol) of 2-bromo-1-(3-methylbut-2-enyl)-5/6-nitro-1H-benzimidazole were dissolved in 8 ml of dimethylformamide and added slowly. The reaction mixture was stirred at 40° C. for 6 hours. The precipitate was filtered off with suction and washed with dimethylformamide. The filtrate was concentrated and partitioned between ethyl acetate and water. The organic phase was dried and concentrated under reduced pressure. The crude mixture was separated on silica gel (eluent: heptane/ethyl acetate, gradient: 3/1 to 1/1). 176 mg (35%) of tert-butyl R-{1-[1-(3-methylbut-2-enyl)-5-nitro-1H-benzimidazol-2-yl]piperidin-3-yl}carbamate and 163 mg (32%) of the desired product were obtained.

LCMS: m/z=430.2 (M+H)$^+$.

d) tert-Butyl R-{1-[6-amino-1-(3-methylbut-2-enyl)-1H-benzimidazol-2-yl]piperidin-3-yl}carbamate

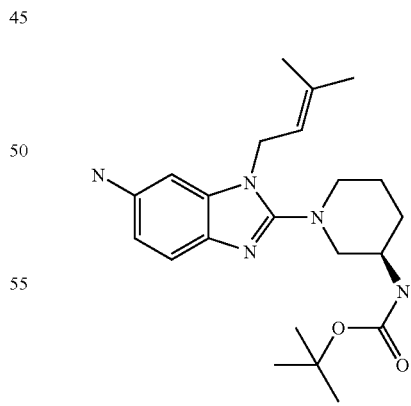

A solution of 163 mg (0.38 mmol) of tert-butyl R-{1-[1-(3-methylbut-2-enyl)-6-nitro-1H-benzimidazol-2-yl]piperidin-3-yl}carbamate in 10 ml of ethanol was added dropwise to a suspension of 106 mg (1.90 mmol) of iron and 18 mg (0.34 mmol) of ammonium chloride in 1 ml of water, and the mixture was boiled at reflux for 3 hours. The catalyst was filtered off and washed with ethanol. The filtrate was concentrated under reduced pressure. 155 mg of the desired product were obtained and were reacted in the next stage without further purification.

MS:m/z=400.3 (M+H)$^+$.

e) tert-Butyl R-{1-[6-benzenesulfonylamino-1-(3-methylbut-2-enyl)-1H-benzimidazol-2-yl]piperidin-3-yl}carbamate

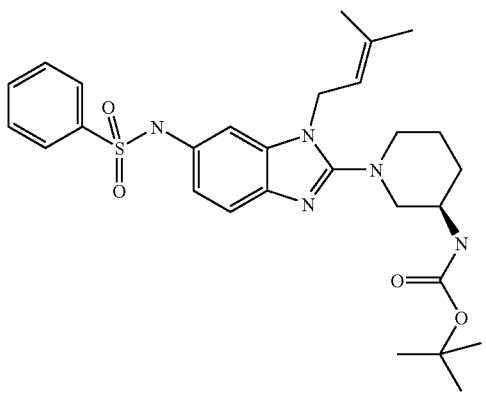

20 mg (0.06 mmol) of cesium carbonate were added to a solution of 50 mg (0.13 mmol) of tert butyl R-{1-[6-amino-1-(3-methylbut-2-enyl)-1H-benzimidazol-2-yl]piperidin-3-yl}carbamate in 5 ml of dimethylformamide, and the mixture was stirred at room temperature for 30 minutes. Subsequently, 22 μl (0.13 mmol) of benzenesulfonyl chloride were added and the mixture was stirred at room temperature for 20 hours. The reaction mixture was partitioned between dichloromethane and water, and the organic phase was dried and concentrated under reduced pressure.

The crude mixture was separated on silica gel (eluent: heptane/ethyl acetate, gradient: 1/1 to 0/1). 43 mg (63%) of the desired compound were obtained.

MS: m/z=540.5 (M+H)$^+$.

f) R-N-[2-(3-Aminopiperidin-1-yl)-1-(3-methylbut-2-enyl)-1H-benzimidazol-6-yl]-benzenesulfonamide trifluoroacetic acid salt

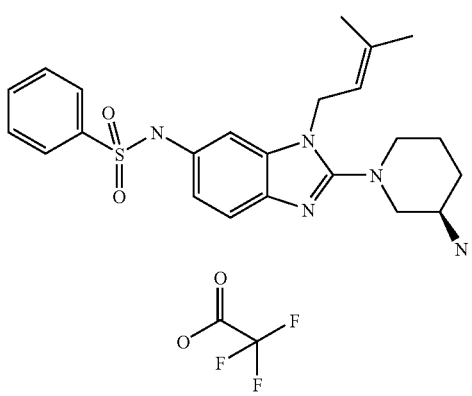

43 mg (0.08 mmol) of tert-butyl R-{1-[6-benzenesulfonylamino-1-(3-methylbut-2-enyl)-1H-benzimidazol-2-yl]piperidin-3-yl}carbamate were dissolved in 182 mg of trifluoroacetic acid and 12 μl of water, and stirred at room temperature for 19 hours. The reaction mixture was admixed with water and freeze-dried. 48 mg of the desired product were obtained in quantitative yield.

MS: m/z=440.4 (M+H)$^+$.

What is claimed is:

1. A method for the reduction of blood sugar levels comprising administering to a patient in need thereof a therapeutically effective amount of a compound of formula I

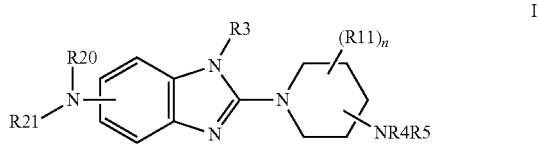

wherein:

R20 and R21 are each independently selected from the group consisting of H, $(C_1-C_6)$-alkylene-$(C_6-C_{10})$-aryl and $S(O)_2$-aryl, wherein the aryl groups are each optionally mono- or poly-substituted by F, Cl, Br, I, CN, $NO_2$, SH, OH, $(C_1-C_6)$-alkyl, O-$(C_1-C_6)$-alkyl or S-$(C_1-C_6)$-alkyl;

R3 is selected from the group consisting of $(C_2-C_{10})$-alkenyl and $(C_1-C_6)$-alkylene-$(C_6-C_{10})$-aryl;

R4 and R5 are each H; and

R11 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O-$(C_1-C_6)$-alkyl, where the alkyl groups are optionally mono- or polysubstituted by F, Cl, Br or I; and n is 0;

or a pharmaceutically acceptable salt thereof useful in the preparation of a pharmaceutical composition for the reduction of blood sugar levels.

2. The method as recited in claim 1 wherein the patient has diabetes.

* * * * *